(12) United States Patent
Jilisen et al.

(10) Patent No.: US 12,326,428 B2
(45) Date of Patent: Jun. 10, 2025

(54) RESIDUAL GAS ANALYZER (71) Applicant: ASML Netherlands B.V., Veldhoven (NL)

(72) Inventors: Reinier Theodorus Martinus Jilisen, Eindhoven (NL); Maarten Jan Heerkens, Waalre (NL); Hendrikus Petrus Kluijtmans, Asten (NL); Robbert Willem Frederik Oosterbaan, Valkenswaard (NL); Antonius Marinus Coenraad Petrus Leonardus Van De Kerkhof, Handel (NL)

(73) Assignee: ASML NETHERLANDS B.V., Veldhoven (NL)

( * ) Notice: Subject to any disclaimer, the term of this patent is extended or adjusted under 35 U.S.C. 154(b) by 83 days.

(21) Appl. No.: 18/032,438

(22) PCT Filed: Sep. 27, 2021

(86) PCT No.: PCT/EP2021/076496
§ 371 (c)(1),
(2) Date: Apr. 18, 2023

(87) PCT Pub. No.: WO2022/083976
PCT Pub. Date: Apr. 28, 2022

(65) Prior Publication Data
US 2023/0384276 A1    Nov. 30, 2023

(30) Foreign Application Priority Data
Oct. 20, 2020   (EP) .................................... 20202743

(51) Int. Cl.
*G01N 33/00* (2006.01)
*G01N 27/64* (2006.01)

(52) U.S. Cl.
CPC ......... *G01N 33/0006* (2013.01); *G01N 27/64* (2013.01)

(58) Field of Classification Search
CPC .... G01N 33/0006; G01N 27/64; G01N 27/62; G01N 27/623; H01J 49/4215; G01M 3/202
(Continued)

(56) References Cited

U.S. PATENT DOCUMENTS 4,562,351 A    12/1985    Atherton et al.
4,963,736 A *  10/1990    Douglas .............. H01J 49/4215
                                                          250/288

(Continued)

FOREIGN PATENT DOCUMENTS

CN        210834044 U     6/2020
DE     102016209878 A1    7/2016
(Continued)

OTHER PUBLICATIONS

International Search Report and Written Opinion of the International Searching Authority directed to International Patent Application No. PCT/EP2021/076496, mailed Jan. 10, 2022; 9 pages.

*Primary Examiner* — Christopher P McAndrew
(74) *Attorney, Agent, or Firm* — Sterne, Kessler, Goldstein & Fox P.L.L.C.

(57) ABSTRACT

Disclosed herein is a residual gas analyser for detecting gas in a vacuum tool, the residual gas analyser comprising: one or more ion sources configured to ionise a gas in the residual gas analyser; one or more detectors configured to detect an ionised gas by the ion source; and one or more gas generating filaments configured to generate gas within the residual gas analyser.

17 Claims, 4 Drawing Sheets

(58) Field of Classification Search
USPC .......................................................... 324/464
See application file for complete search history.

(56) References Cited

U.S. PATENT DOCUMENTS

| | | | | |
|---|---|---|---|---|
| 7,312,444 | B1* | 12/2007 | Willougbhy | ............ H01J 49/24 |
| | | | | 250/292 |
| 2002/0092979 | A1* | 7/2002 | McCauley | ......... G01N 33/0006 |
| | | | | 250/282 |
| 2013/0148200 | A1 | 6/2013 | Ehm et al. | |

FOREIGN PATENT DOCUMENTS

| | | |
|---|---|---|
| EP | 0 676 792 A2 | 10/1995 |
| GB | 863999 A | 3/1961 |
| IT | TO20090513 A1 | 1/2011 |
| KR | 10-1983293 B1 | 5/2019 |
| WO | WO 2014/118122 A2 | 8/2014 |
| WO | WO 2019/172433 A1 | 9/2019 |

* cited by examiner

RESIDUAL GAS ANALYZER

CROSS-REFERENCE TO RELATED APPLICATIONS

This application claims priority of EP application 20202743.9 which was filed on 20 Oct. 2020, and which is incorporated herein in its entirety by reference.

FIELD

The present invention relates to a residual gas analyser for use with a vacuum tool. More particularly, the techniques disclosed herein relate to the provision of a residual gas analyser that may have one or more of self-diagnostic capabilities, improved cleaning and/or conditioning capabilities and improved calibration capabilities.

BACKGROUND

A lithographic apparatus is a machine that applies a desired pattern onto a substrate, usually onto a target portion of the substrate. A lithographic apparatus can be used, for example, in the manufacture of integrated circuits (ICs). In the manufacture of ICs, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning" direction) while synchronously scanning the substrate parallel or anti-parallel to this direction.

A theoretical estimate of the limits of pattern printing can be given by the Rayleigh criterion for resolution as shown in equation (1):

$$CD = k_1 * \frac{\lambda}{NA} \quad (1)$$

where $\lambda$ is the wavelength of the radiation used, NA is the numerical aperture of the projection system used to print the pattern, $k_1$ is a process dependent adjustment factor, also called the Rayleigh constant, and CD is the feature size (or critical dimension) of the printed feature. It follows from equation (1) that reduction of the minimum printable size of features can be obtained in three ways: by shortening the exposure wavelength $\lambda$, by increasing the numerical aperture NA or by decreasing the value of $k_1$.

In order to shorten the exposure wavelength and, thus reduce the minimum printable size, it has been proposed to use an extreme ultraviolet (EUV) radiation source. EUV radiation is electromagnetic radiation having a wavelength within the range of 4-20 nm, for example within the range of 13-14 nm, for example within the range of 4-10 nm such as 6.7 nm or 6.8 nm. Possible sources include, for example, laser-produced plasma sources, discharge plasma sources, or sources based on synchrotron radiation provided by an electron storage ring.

EUV radiation may be produced using a plasma. A radiation system for producing EUV radiation may include a laser for exciting a fuel to provide the plasma, and a source collector module for containing the plasma. The plasma may be created, for example, by directing a laser beam at a fuel, such as droplets of a suitable material (e.g., tin), or a stream of a suitable gas or vapor, such as Xe gas or Li vapor. The resulting plasma emits output radiation, e.g., EUV radiation, which is collected using a radiation collector. The radiation collector may be a mirrored normal incidence radiation collector, which receives the radiation and focuses the radiation into a beam. The source collector module may include an enclosing structure or chamber arranged to provide a vacuum environment to support the plasma. Such a radiation system is typically termed a laser produced plasma (LPP) source.

In an EUV vacuum tool, such as an EUV lithographic apparatus and/or an EUV source, a very high level of cleanliness needs to be maintained. In particular, any contaminant gasses within an EUV vacuum tool may damage optical components within the EUV vacuum tool. The tolerable level of contaminant gasses in an EUV vacuum tool is lower than in most other vacuum tool applications.

There is a general need to improve the determination and monitoring of contaminant gasses within vacuum tools, such as an EUV vacuum tool.

SUMMARY

According to a first aspect of the invention, there is provided a residual gas analyser for detecting gas in a vacuum tool, the residual gas analyser comprising: one or more ion sources configured to ionise a gas in the residual gas analyser; one or more detectors configured to detect an ionised gas by the ion source; and one or more gas generating filaments configured to generate gas within the residual gas analyser. The gas generating filament may comprise one or more of Rhenium, Tungsten or Iridium.

According to a second aspect of the invention, there is provided a vacuum tool comprising one or more residual gas analysers according to the first aspect.

According to a third aspect of the invention, there is provided a method of testing a residual gas analyser, the method comprising: using a gas generating filament to generate gas within the residual gas analyser; operating the residual gas analyser to detect the generated gas; and determining the performance of the residual gas analyser in dependence on the detection of the gas.

According to a fourth aspect of the invention, there is provided a method of conditioning a residual gas analyser, the method comprising: radiating the inside of a sample chamber of the residual gas analyser by radiation generated by a gas generating filament in the sample chamber; and de-gassing the sample chamber.

According to a fifth aspect of the invention, there is provided a method of calibrating a residual gas analyser, the method comprising: using a gas generating filament to generate gas within the residual gas analyser; operating the residual gas analyser to detect the generated gas; and calibrating the residual gas analyser in dependence on the detected gas.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF FIGURES

The accompanying drawings, which are incorporated herein and form part of the specification, illustrate the present invention and, together with the description, further serve to explain the principles of the invention and to enable a person skilled in the relevant art(s) to make and use the invention.

DESCRIPTION OF EMBODIMENTS

This specification discloses one or more embodiments that incorporate the features of this invention. The disclosed embodiment(s) merely exemplify the invention. The scope of the invention is not limited to the disclosed embodiment(s). The invention is defined by the claims appended hereto. The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
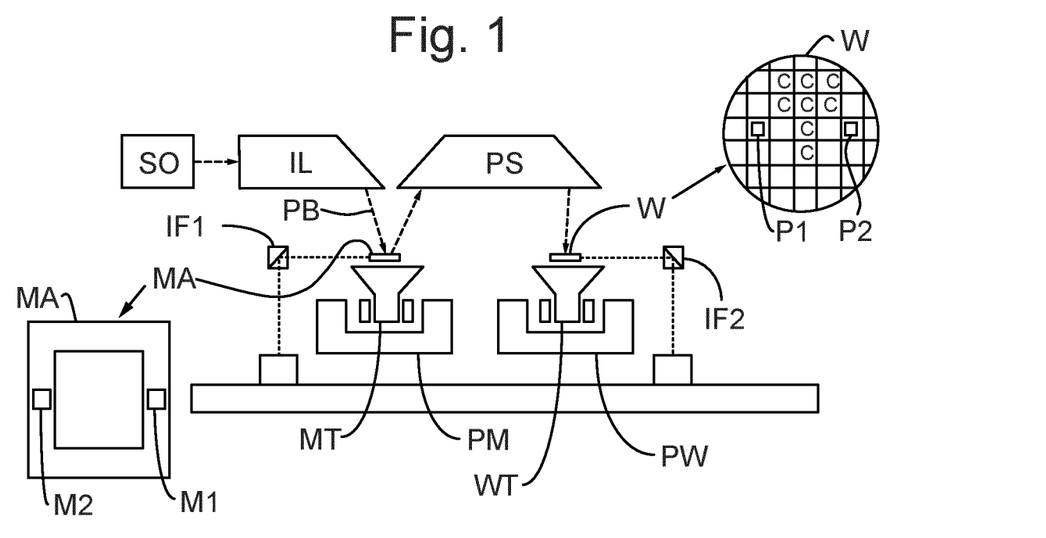
FIG. 1 schematically depicts a known lithographic apparatus.

FIG. 1 schematically shows a lithographic apparatus LAP including a source collector module SO. The apparatus comprises: an illumination system (illuminator) IL configured to condition a radiation beam B (e.g., EUV radiation); a support structure (e.g., a mask table) MT constructed to support a patterning device (e.g., a mask or a patterning device) MA and connected to a first positioner PM configured to accurately position the patterning device; a substrate table (e.g., a wafer table) WT constructed to hold a substrate (e.g., a resist-coated wafer) W and connected to a second positioner PW configured to accurately position the substrate; and a projection system (e.g., a reflective projection system) PS configured to project a pattern imparted to the radiation beam PB by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure MT comprises a part for receiving and holding the patterning device MA in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system.

The term "patterning device" should be broadly interpreted as referring to any device that can be used to impart a radiation beam with a pattern in its cross-section such as to create a pattern in a target portion of the substrate. The pattern imparted to the radiation beam may correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The projection system, like the illumination system, may include various types of optical components, such as refractive, reflective, magnetic, electromagnetic, electrostatic or other types of optical components, or any combination thereof, as appropriate for the exposure radiation being used, or for other factors such as the use of a vacuum. It may be desired to use a vacuum for EUV radiation since other gases may absorb too much radiation. A vacuum environment may therefore be provided to the whole beam path with the aid of a vacuum vessel and vacuum pumps.

As here depicted, the apparatus is of a reflective type (i.e., employing a reflective mask and reflective optics in the illuminator IL and projection system PS).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

Referring to FIG. 1, the illuminator IL receives an EUV radiation beam from the EUV source SO. Methods to produce EUV radiation include, but are not necessarily limited to, converting a material into a plasma state that has at least one chemical element, e.g., xenon, lithium, or tin, with one or more emission lines in the EUV range. In one such method, often termed laser-produced plasma ("LPP"), the required plasma can be produced by irradiating a fuel, such as a droplet of material having the required line-emitting element, with a laser beam. The EUV source SO may be part of an EUV radiation source including a laser, not shown in FIG. 1, for providing the laser beam exciting the fuel. The resulting plasma emits output radiation, e.g., EUV radiation, which is collected using a radiation collector, disposed in the EUV source.

The laser and the EUV source may be separate entities, for example when a $CO_2$ laser is used to provide the laser beam for fuel excitation. In such cases, the radiation beam is passed from the laser to the EUV source with the aid of a beam delivery system comprising, for example, suitable directing mirrors and/or a beam expander. The laser and a fuel supply may be considered to comprise an EUV radiation source.

The illuminator IL may comprise an adjuster for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as facetted field and pupil mirror devices. The illuminator may be used to condition the radiation beam, to have a desired uniformity and intensity distribution in its cross-section.

The radiation beam PB is incident on the patterning device (e.g., mask) MA, which is held on the support structure (e.g., mask table) MT, and is patterned by the patterning device. The patterning device MA may be positioned using first positioning device such as interferometer IF1 and mask alignment marks M1, M2. After being reflected from the patterning device (e.g., mask) MA, the patterned radiation beam PB passes through the projection system PS, which focuses the beam onto a target portion C of the substrate W. With the aid of the second positioning device such as interferometer IF2 and substrate alignment marks P1, P2 (e.g., using interferometric devices, linear encoders or capacitive sensors), the substrate table WT can be moved accurately, e.g., so as to position different target portions C in the path of the radiation beam PB.

The depicted apparatus could be used in at least one of the following modes:

1. In step mode, the support structure (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed.

2. In scan mode, the support structure (e.g., mask table) MT and the substrate table WT are scanned synchronously while a pattern imparted to the radiation beam is projected onto a target portion C (i.e., a single dynamic exposure). The velocity and direction of the substrate table WT relative to the support structure (e.g., mask table) MT may be determined by the (de-)magnification and image reversal characteristics of the projection system PS.

3. In another mode, the support structure (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes a programmable patterning device, such as a programmable mirror array of a type as referred to above.

Figure 2:
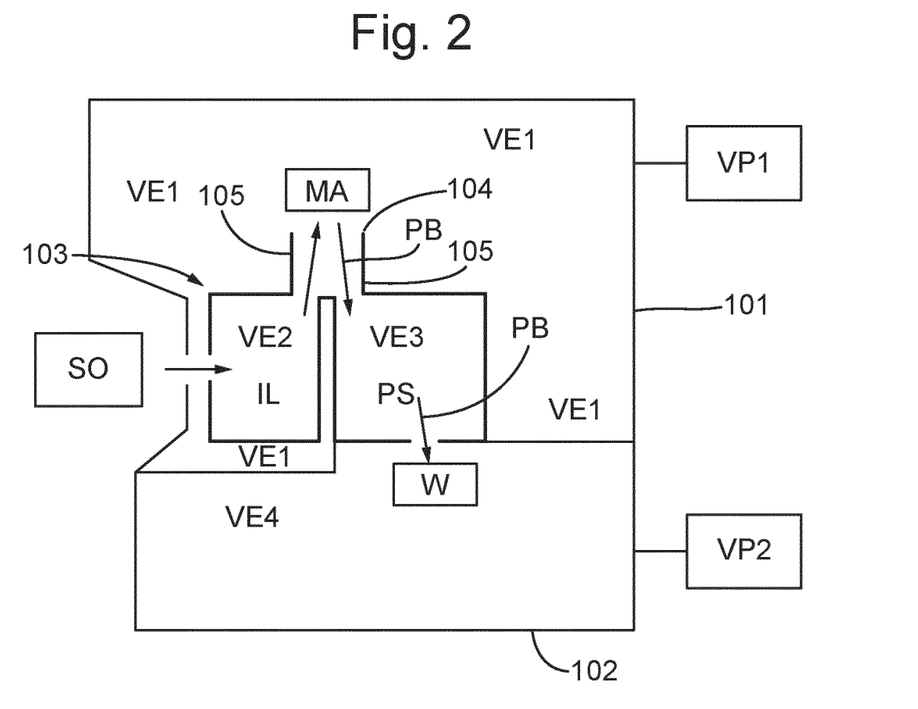
FIG. 2 shows pressure zones of a known lithographic apparatus.

FIG. 2 schematically shows an known apparatus. The apparatus of FIG. 2 includes a first chamber 101 that contains an illumination system IL as well as a projection system PS. The illumination system IL is configured to condition a radiation beam received from source SO, and the projection system PS is configured to project a patterned radiation beam PB onto a target portion of a substrate W. First chamber 101 also contains a patterning device support constructed to support the patterning device MA, the patterning device MA being capable of imparting a radiation beam with a pattern in its cross-section to form the patterned radiation beam. A second chamber 102 contains the wafer stage of which for clarity only the substrate W is shown.

FIG. 2 shows how the apparatus may be divided into four different vacuum environments VE1 to VE4. First chamber 101 defines a first vacuum environment VE1 that encloses the patterning device stage of which, for clarity, only the patterning device MA is shown. First chamber 101 also includes a separator construction 103 that defines two further vacuum environments: VE2 housing the illumination system IL, and VE3 housing the projection system PS. Vacuum environments VE2 and VE3 could be further divided. Separator construction 103 includes a sleeve 105 having an aperture 104 for passing the projection beam PB from the illumination system IL to patterning device MA, and for passing the patterned radiation beam from patterning device MA to the projection system PS. The sleeve 105 also serves to force the gas flow downwards (ie away from the patterning device) and to maintain the gas flow even to avoid disturbance of the EUV radiation intensity. Possibly the sleeve may taper towards the patterning device MA. Second chamber 102 defines a vacuum environment VE4 that the wafer stage (of which for clarity only substrate W is shown). Vacuum environments VE1 and VE2 are formed and maintained by respective vacuum vessels and vacuum pumps VP1 and VP2, which can also be a plurality of vacuum pumps.

As is shown in FIG. 2 vacuum pump VP1 maintains vacuum environment VE1 at a lower pressure than vacuum environments VE2 and VE3. Clean gas (e.g., hydrogen, helium, nitrogen, oxygen or argon) is injected into vacuum environments VE2 and VE3 using gas injectors (not shown). The vacuum pumps VP1, VP2 as such are known to the skilled person, and may be coupled to the apparatus in various ways.

The separator construction 103 can be arranged in various ways, and may include, for example, a sleeve 105 extending towards the patterning device MA at the end of which sleeve 105 is provided the projection beam aperture 104 extend towards the patterning device MA. The sleeve 105 bearing the aperture 104 may have a tapered cross-section.

Described above, with reference to FIGS. 1 and 2, are components of a lithographic apparatus that perform lithographic processes with EUV radiation.

The performance of a vacuum tool is dependent on how clean each vacuum environment within the vacuum tool is. This is particularly important for an EUV vacuum tool, such as an EUV lithographic apparatus, in which very clean vacuum environments are required over a large dynamic range. Any contaminant gasses within a vacuum environment may severely damage any optical components in the vacuum environment. A contaminant gas as referred to herein may be any gas that, when present in a quantity higher than a tolerance level for the gas, may potentially be detrimental to any aspect of the performance of a vacuum tool. The levels and/or types of gasses present in each of the vacuum environments therefore needs to be closely monitored. The availability of the EUV vacuum tool is dependent on the state of the vacuum environments because the EUV beam should not be switched on if the levels of any gasses present are not within the operational specification (i.e. below maximum tolerable levels). When the levels of any gasses present are not within the operational specification, the vacuum environments of the EUV vacuum tool need to be reconditioned in order to prevent excessive damage to the optical components, or other components, occurring.

The gas types, and levels, within a vacuum environment of an EUV vacuum tool may be monitored by a residual gas analyser (RGA). An RGA is a mass spectrometer for process control and contamination monitoring of a vacuum environment. RGAs may be used to determine if an EUV vacuum tool is ready for exposure (i.e. the EUV beam may be switched on), monitor the levels of contaminant gasses within the EUV vacuum tool and detect any vacuum leaks.

A known implementation of an RGA comprises an ion source, a sample chamber containing rarified gas, an ion accelerator and an ionization chamber. The ion source may include an ion generating filament that is an electron emitter. The ion generating filament may be a cathode. Electrons from the ion source are accelerated towards an anode. The electrons enter the sample chamber, through one or more openings in the walls of the sample chamber, and ionize gas molecules within the sample chamber. The ion accelerator draws the resulting ions out of the sample chamber and focusses them into a beam of ions that are injected into the ionization chamber. The ionization chamber may comprise one or more mass analysis instruments for analysing and/or detecting the ions. The RGA may, for example, generate and output a spectrum showing the masses and concentrations of the detected ions. An RGA therefore allows the detection, measurement and monitoring of gases within a vacuum environment.

As described earlier with reference to FIG. 2, an EUV vacuum tool may comprise a plurality of vacuum environments. Each vacuum environment within the EUV vacuum tool may comprise an RGA so that the EUV vacuum tool comprises a plurality of RGAs. A single vacuum environment within an EUV vacuum tool may comprise a plurality of RGAs. For example, if a vacuum environment within an EUV vacuum tool comprises more than one set of optical components, a separate RGA may be positioned close to each set of optical components.

The use of one or more RGAs in an EUV vacuum tool therefore allows the detection, measurement and monitoring of the gases within the EUV vacuum tool. In response to the gas detection, measurement and/or monitoring, reconditioning operations, and/or any other appropriate actions, may be performed if contaminant gasses are detected and/or the measured levels contaminant gasses are higher than an tolerable level.

A number of problems can be identified with known implementations of RGAs in EUV vacuum tools.

It may be difficult to determine if an RGA is operating correctly or if the RGA is faulty. The consequences of incorrect operation of an RGA may include, for example, reduced availability of the EUV vacuum tool and the optical components of the EUV vacuum tool being damaged by contaminant gasses.

Another problem with known RGAs is that it may be difficult to clean the inside of the RGA to the high standard required for EUV vacuum tool applications.

Another problem with known RGAs is that it may be difficult to calibrate the RGA.

Embodiments provide a new RGA for use with vacuum tools. The RGA according to embodiments may be particularly appropriate for use with an EUV vacuum tool, such as an EUV lithographic apparatus, and solve one or more of the above problems.

Figure 3:
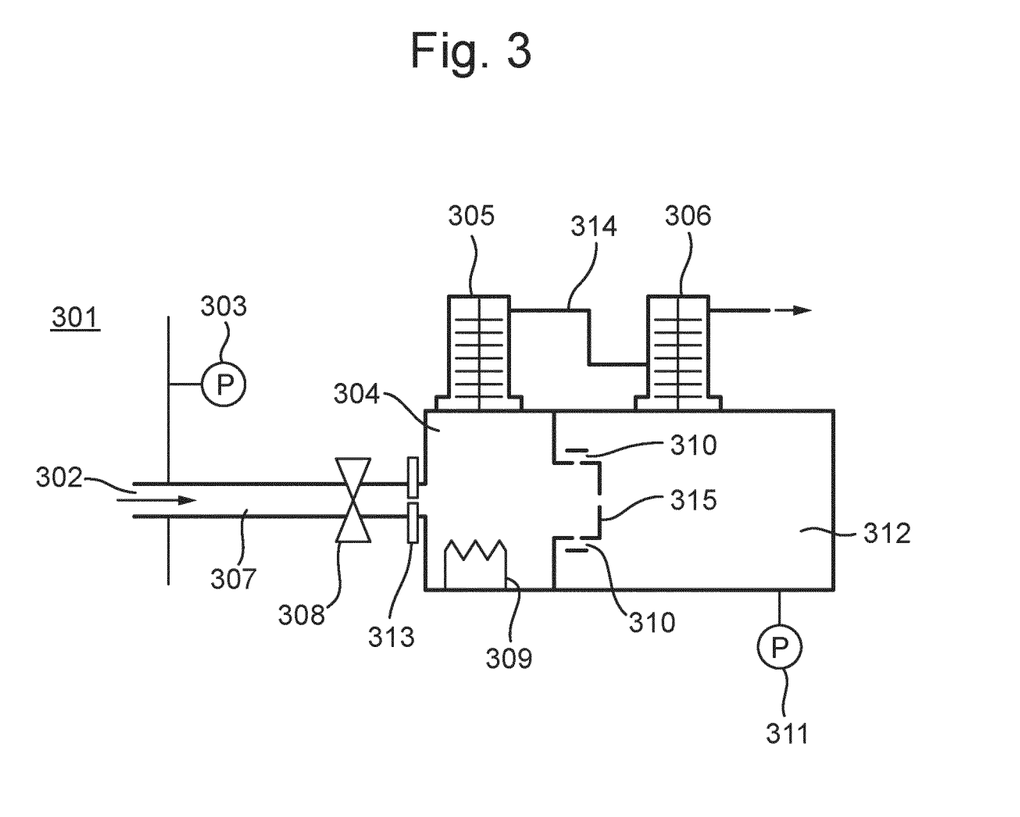
FIG. 3 shows a RGA according to an embodiment.

FIG. 3 shows an RGA according to an embodiment. The RGA comprises a sample chamber 304, ion accelerator 315 and an ionization chamber 312.

The ionization chamber 312 comprises ion sources 310. The ion sources 310 may be ion generating filaments that are arranged to emit electrons. Each ion generating filament may be a cathode. The ionization chamber 312 may be arranged so that electrons from each ion source 310 are accelerated towards an anode. Although two ion sources 310 are shown in FIG. 3, embodiments also include the use of only one ion source 310, or more than two ion sources 310. Preferably, there are a plurality of ion sources 310 so that the operational lifetime of the RGA is not dependent on only one ion source 310.

The ionization chamber 312 may comprise one or more of a quadruple mass filter, a Faraday Cup, a Secondary Electron Multiplier detector and/or one or more other mass analysis instruments, for detecting and/or analysing the ions. Although not shown in FIG. 3, the RGA may comprise a computing system for generating and outputting analysis results. For example, the analysis results may comprise a spectrum showing the masses and concentrations of the detected ions.

The RGA may comprise a first vacuum pump 305 arranged to pump gas out of the sample chamber 304. The RGA may also comprise a second vacuum pump 306 arranged to pump gas out of the ionization chamber 312. There may be an interstage line 314 between the first vacuum pump 305 and the second vacuum pump 306. The first vacuum pump 305 and second vacuum pump 306 are respectively arranged to generate and maintain substantial vacuum conditions in the sample chamber 304 and the ionization chamber 312. The extent of the vacuum in the sample chamber 304 and ionization chamber 312 may be the same or different. In particular, the pressure may be lower in the ionization chamber 312 than the sample chamber 304. In an alternative implementation according to an embodiment, there is only a single vacuum pump for generating and maintaining substantial vacuum conditions in the sample chamber 304 and the ionization chamber 312. The RGA may comprise one or more pressure gauges 311 for measuring the pressure within the ionization chamber 312.

The RGA may comprise a sample tube 307. An end 302 of the sample tube 307 is in fluid communication with the inside environment of a vacuum chamber 301 of a vacuum tool, such as a EUV vacuum tool. There may be a pressure gauge 303 for measuring the pressure within the vacuum chamber 301. The other end of the sample tube 307 is in fluid communication with the inside of the sample chamber 304. The sample tube 307 may comprise a valve 308 arranged to control the flow of gasses through the sample tube 307. There may be an orifice 313 at the interface between the sample tube 307 and the sample chamber 304. The sample chamber 304 may be operated at a lower pressure than the vacuum chamber 301 and the orifice 313 may help to support the pressure difference between the sample tube 307 and the sample chamber 304.

The sample chamber 304 may comprise one or more gas generating filaments 309. Each gas generating filament 309 in the sample chamber 304 may be configured so that it can be heated. A property of each gas generating filament 309 may be that it releases a gas and/or photons when it is heated. Each gas generating filament 309 may release a gas without the gas generating filament 309 melting. That is to say, each gas generating filament 309 may be a material that sublimes.

Each gas generating filament 309 in the sample chamber 304 may comprise, for example, Rhenium (Re). A Rhenium gas generating filament 309 may release Rhenium gas when it is heated. Each Rhenium gas generating filament 309 may be heated to about 1800° C. so that Rhenium gas evaporates from the Rhenium gas generating filament 309. Each Rhenium gas generating filament 309 may therefore release a gas without the Rhenium gas generating filament 309 melting (the melting point of Rhenium is about 3186° C.). Each Rhenium gas generating filament 309 may also be heated to about 1800° C. so that it emits high energy photons. A Rhenium gas generating filament 309 may be used when inert gasses, hydrocarbons, $H_2$, halogens and/or freons are present. The vaporization of a Rhenium gas generating filament 309 may limit its service life.

The sample chamber 304 may be separated from the ionization chamber 312 by a wall that comprises very small openings. The openings in the wall are configured such as to allow ions to flow from the sample chamber 304 and into the ionization chamber 312.

Although not shown in FIG. 3, one or more pressure gauges may be provided for measuring and monitoring the pressure in the sample chamber 304.

The following is a description of a first operational mode of the RGA shown in FIG. 3 according to an embodiment. In the described first operational mode, the RGA may be operated with an EUV vacuum tool in order to detect, and measure, the presence of any gasses in a vacuum chamber 301 of the EUV vacuum tool.

The valve 308 may be open so that any gas within the vacuum chamber 301 may flow through the sample tube 307, through the orifice 313 and into the sample chamber 304. The sample chamber 304 may be a lower pressure than the vacuum chamber 301 and so opening the valve 308 does not cause gas to flow from the sample chamber 304 into the vacuum chamber 301.

The sample chamber 304 may therefore contain gas received from the vacuum chamber 301. The ion sources 310 may emit electrons into the sample chamber 304. The emitted electrons may pass through one or more openings in the walls of the sample chamber 304. At least some of the gas within the sample chamber 304 may be ionised by the emitted electrons. The ions may be accelerated, by the ion accelerator 315, into an ion beam that is injected into the ionization chamber 312. A detector in the ionization chamber 312 may detect the ions. An output from the RGA may comprise, for example, a spectrum showing the masses and/or concentrations of the detected ions, and/or measurements of partial pressure levels of the gasses present in the vacuum chamber 301.

Accordingly, the RGA may detect the presence and/or relative concentration of any gasses that are present in the vacuum chamber 301. In particular, the presence of any contaminant gasses may be detected and their concentration and/or partial pressure levels monitored.

When the RGA is used to detect and monitor gasses within the vacuum chamber 301 as described above, the gas generating filament 309 in the sample chamber 304 may not be activated (i.e. heated/excited). The gas generating filament 309 in the sample chamber 304 does not therefore release any gas or photons into the sample chamber 304. Substantially the only gasses present within the sample chamber 304 may therefore be those received from the vacuum chamber 301 of the vacuum tool. Alternatively, when the RGA is used to detect and monitor gasses within the vacuum chamber 301 as described above, the gas generating filament 309 may also be activated (i.e. heated/excited) so that it releases a gas. The sample chamber may therefore comprise both gasses received from the vacuum tool and also gas from the gas generating filament 309. The RGA may detect the presence and/or relative concentration of all of these gasses.

The following is a description of a second operational mode of the RGA shown in FIG. 3 according to an embodiment. In the second operational mode, the gas generating filament 309 in the sample chamber 304 may advantageously be used to test the performance of the RGA.

The valve 308 may be closed so that the sample chamber 304 is isolated from the external environment of the RGA. When the RGA is comprised by an EUV vacuum tool, closing the valve 308 isolates the sample chamber 304 from the vacuum chamber 301 of the EUV vacuum tool. The gas generating filament 309 may then be heated so that it releases a gas. The gas generating filament 309 may be heated by an electric current flowing through it. The released gas may be evaporated gas from the heated gas generating filament 309. If the gas generating filament 309 is a Rhenium gas generating filament 309, the gas generating filament 309 may release Rhenium gas.

The RGA may then be operated as described above for the first operational mode, except that the valve 308 may be closed so that substantially the only gas in the sample chamber 304 is the released gas by the gas generating filament 309. That is to say, the ion sources 310 may emit electrons that ionize the gas in the sample chamber 304. The ion accelerator 315 may then accelerate the ions and inject an ion beam into the ionization chamber 312. The ions may then be detected and the level(s) of the gas, or gasses, that are present in the sample chamber 304 determined.

The second operational mode may be used to test the performance of the RGA. For example, if the gas generating filament 309 releases Rhenium gas when it is heated, an expected analysis output from the RGA may be a spectrum with substantial peaks corresponding to the mass numbers 185 and 187. A comparison of an actual analysis output from the RGA and the expected analysis output of the RGA may be used to determine the performance of the RGA. In particular, the accuracy, reliability and/or any other performance metrics of the RGA may be determined.

The generation of a gas within the sample chamber 304 by the gas generating filament 309 therefore enables the RGA with a self-test/diagnosis capability. With an RGA according to an embodiment, if any results are generated that may indicate that the RGA is malfunctioning, the RGA may be quickly tested to determine if it is operating correctly. The RGA test may be performed without any disassembly of the RGA, or a vacuum tool that comprises the RGA. In particular, the conditions within the vacuum chamber 301 of an EUV vacuum tool may remain substantially unchanged when the RGA is tested. This is a substantial advantage over known RGAs without such self-test/diagnosis capability. If a potential malfunction is detected with a known RGA then it may be necessary to replace the RGA and this may cause a long downtime of an EUV vacuum tool. The gas generating filament 309 may therefore improve the availability of the RGA and consequently a vacuum tool that comprises the RGA.

Another advantage of the gas generating filament 309 in the sample chamber 304 is that it additionally may be used to calibrate the RGA. If the gas generating filament 309 material generates a gas with a stable spectrum for specific pressures, the secondary electron multiplier detector voltage may be determined in a ready for exposure process to improve the accuracy of pressure measurements.

The following is a description of a third operational mode of the RGA shown in FIG. 3 according to an embodiment. In the third operational mode, the gas generating filament 309 in the sample chamber 304 may advantageously be used to condition the sample chamber 304 of the RGA.

The valve 308 may be closed so that the sample chamber 304 is isolated from the vacuum chamber 301. The gas generating filament 309 may then be heated. The gas generating filament 309 may be heated by an electric current flowing through it. When the gas generating filament 309 is heated, the gas generating filament 309 may emit high energy photons. The effect of radiating the inner walls of the sample chamber 304 with the photons may be that any contaminants that may be present on the inner walls of the sample chamber 304 are released. The first vacuum pump 305 may then be used to de-gas the sample chamber 304 to thereby remove the released contaminants from the inner walls of the sample chamber 304. The gas generating filament 309 may therefore be used to clean the inside of the sample chamber 304. The cleaning operation may be performed at the point of manufacture of the RGA and/or when the RGA is comprised by a vacuum tool.

In known RGAs, the ion sources in the ionization chamber may alternatively be used to radiate the inner walls of the sample chamber prior to de-gassing. However, a disadvantage of this approach may be that the increased use of the ion sources, and/or the use of a high current in the ion sources, reduces the lifetime of the ion sources.

Another advantage of the gas generating filament 309 is that it may be used to heat up the RGA from the inside of the sample chamber 304. This may be faster and/or more efficient than known techniques for heating, or otherwise conditioning, the RGA as may be required.

As described earlier, an EUV vacuum tool may comprise a plurality of vacuum environments. The vacuum environments may differ in their maximum tolerable pressures. The vacuum environments may also differ in the maximum tolerable levels of contaminant gasses. One or more RGAs according to embodiments may be used to monitor the pressures and gas levels in each vacuum environment in the vacuum tool.

The RGAs may be operated over a range of pressures. The specific pressures with each RGA may depend on the vacuum environment that the RGA is monitoring and the detection requirements of the RGA. For example, the pressure of the vacuum chamber 301 that the RGA is monitoring may be, for example, in the range 30 to 60 millibar. The pressure in the sample chamber 304 may be, for example, in the range 4 to 10 microbar. The pressures in the ionization chamber 312 may be the same as in the sample chamber 304 and/or at lower pressures. There may be different regions of the ionization chamber 312 and different pressures within each region. For example, the parts of the ionization chamber 312 that comprises the ion sources 310 may be at the same pressure as the sample chamber 304. However, the part of the ionization chamber 312 that comprises the mass filter and/or detector may be, for example, in the range 1 to 20 nanobar, and preferably less than 5 nanobar.

An RGA according to an embodiment may be used in any part of any type of vacuum tool. In particular, the RGA may be used in a radiation source such as an EUV source. The EUV source may be used with an EUV vacuum tool, such as an EUV lithographic apparatus.

Figure 4:
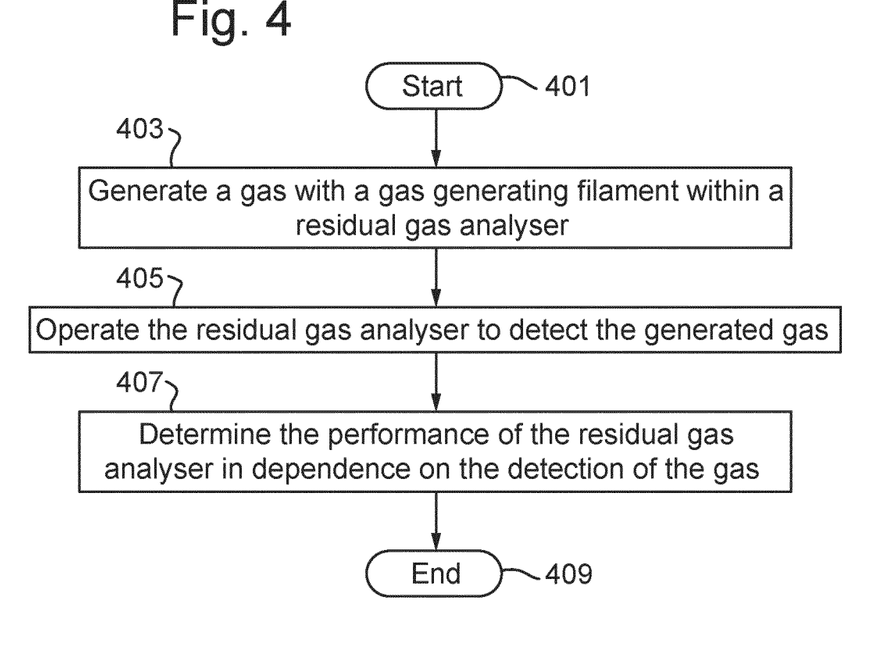
FIG. 4 is a flowchart of a method according to an embodiment.

FIG. 4 is a flowchart of a method of testing a residual gas analyser according to an embodiment.

In step 401, the process starts.

In step 403, a gas generating filament is used to generate gas within the residual gas analyser.

In step 405, the residual gas analyser is operated to detect the generated gas.

In step 407, the performance of the residual gas analyser is determined in dependence on the detection of the gas.

In step 409, the process ends.

Figure 5:
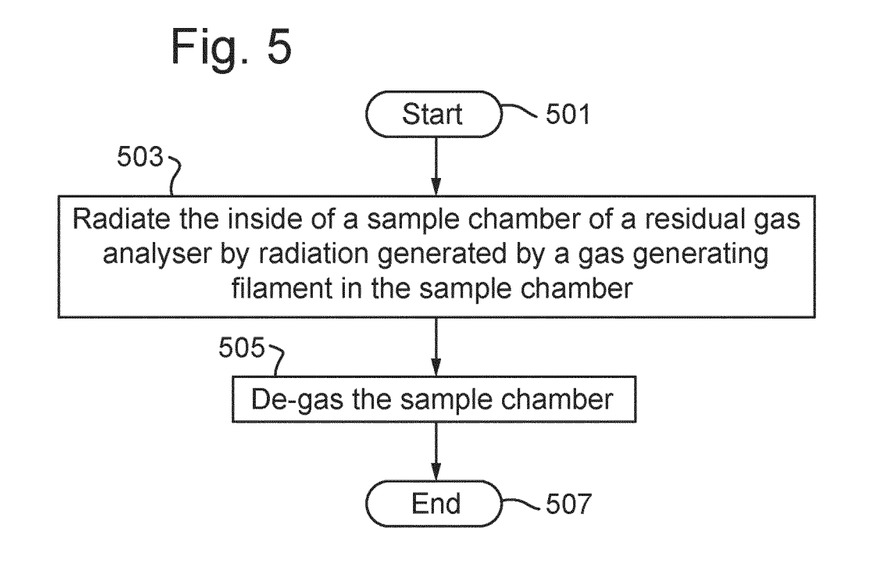
FIG. 5 is a flowchart of a method according to an embodiment.

FIG. 5 is a flowchart of a method of conditioning a residual gas analyser according to an embodiment.

In step 501, the process starts.

In step 503, the inside of a sample chamber of the residual gas analyser is radiated by radiation generated by a gas generating filament in the sample chamber.

In step 505, the sample chamber is de-gassed.

In step 507, the process ends.

Figure 6:
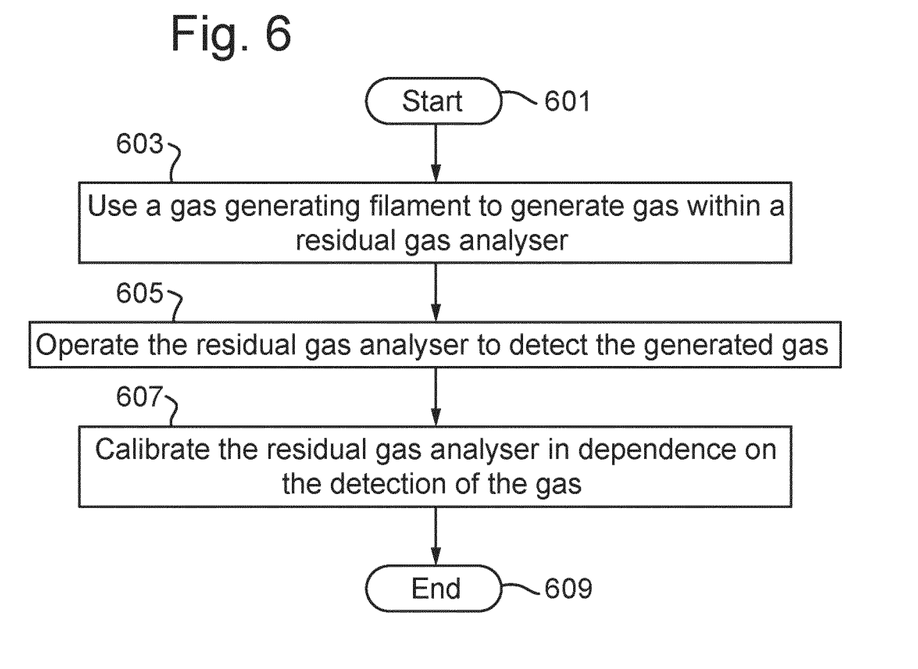
FIG. 6 is a flowchart of a method according to an embodiment.

FIG. 6 is a flowchart of a method of calibrating a residual gas analyser according to an embodiment.

In step 601, the process starts.

In step 603, a gas generating filament is used to generate gas within the residual gas analyser.

In step 605, the residual gas analyser is operated to detect the generated gas.

In step 607, the residual gas analyser is calibrated in dependence on the detected gas.

In step 609, the process ends.

Embodiments include a number of modifications to the techniques described above.

For example, the gas generating filament 309 in the sample chamber 304 may alternatively be made from $Y_2O_2$/Iridium or Tungsten.

A $Y_2O_2$/Iridium gas generating filament 309 may be heated to about 1300° C. so that it releases a gas and/or photons. A $Y_2O_2$/Iridium gas generating filament 309 may be used, for example, when inert gasses, air/$O_2$, NOx and/or SOx are present. A $Y_2O_2$/Iridium gas generating filament 309 may be relatively insensitive to high concentrations of $O_2$. However, a $Y_2O_2$/Iridium gas generating filament's 309 service life may be reduced if halogens are present. Some CO/CO2 may be generated when $O_2$ or $H_2O$ is present.

A Tungsten gas generating filament 309 may be heated to about 1800° C. so that it releases a gas and/or photons. A Tungsten gas generating filament 309 may be used, for example, when inert gasses, $H_2$, halogens and/or freons are present. A Tungsten gas generating filament's 309 service life may be reduced if $O_2$ is present. Some $CO/CO2$ may be generated when $O_2$ or $H_2O$ is present. The presence of Carbon may increase the brittleness of a Tungsten gas generating filament 309.

The use of Rhenium gas generating filament 309 may be preferred because it has a higher vapour pressure than Iridium or Tungsten. However, Iridium or Tungsten may be preferred because they may have a longer operational lifetime than Rhenium.

The gas generating filament 309 in the sample chamber 304 may comprise substantially only one element, for example it may be substantially pure Rhenium. Alternatively, the gas generating filament 309 may be an alloy that comprises more than one element. For example, the gas generating filament 309 in the sample chamber 304 may comprise more than one of Rhenium, Iridium, Tungsten and/or other elements/compounds.

In FIG. 3, there is an interstage line 314 between the first vacuum pump 305 and the second vacuum pump 306. Embodiments also include there being no interstage line 314 between the first vacuum pump 305 and the second vacuum pump 306. The RGA is not restricted to comprising two vacuum pumps as shown in FIG. 3. The RGA may alternatively comprise a single pump with an interstage line so that the same pump may de-gas both the sample chamber 304 and the ionization chamber 312.

Embodiments include the following numbered clauses:

1. A residual gas analyser for detecting gas in a vacuum tool, the residual gas analyser comprising: one or more ion sources configured to ionise a gas in the residual gas analyser; one or more detectors configured to detect an ionised gas by the ion source; and one or more gas generating filaments configured to generate gas within the residual gas analyser.
2. The residual gas analyser according to clause 1, further comprising: a sample chamber configured to receive a gas from the vacuum tool; and an ionisation chamber configured to receive ionised gas from the sample chamber.
3. The residual gas analyser according to clause 2, wherein: the sample chamber comprises the one or more gas generating filaments; the ionisation chamber comprises the one or more ion sources and the one or more detectors; and each ion source is arranged to emit ions into the sample chamber.
4. The residual gas analyser according to any preceding clause, wherein each ion source is configured to emit electrons.
5. The residual gas analyser according to any preceding clause, wherein each gas generating filament comprises one or more of Rhenium, Tungsten or Iridium.
6. The residual gas analyser according to any preceding clause, wherein each gas generating filament is configured so that it is heatable; and each gas generating filament releases gas when it is heated.
7. The residual gas analyser according to any clause 6, wherein each gas generating filament is configured so that it is heatable by an electric current.
8. The residual gas analyser according to clauses 2, or any clause dependent thereon, further comprising: a sample tube configured to provide a flow path of gas from the vacuum tool to the sample chamber; and a valve in the flow path configured to control the flow of gas through the sample tube.
9. The residual gas analyser according to any preceding clause, wherein at least one detector comprises a mass analysis instrument.
10. The residual gas analyser according to any preceding clause, wherein at least one detector comprises one or more of a quadruple mass filter, a Faraday cup, a Secondary Electron Multiplier detector.
11. The residual gas analyser according to any preceding clause, wherein the ion source comprises at least two ion generating filaments.
12. The residual gas analyser according to any preceding clause, further comprising a vacuum pump system configured to generate substantial vacuum conditions in the residual gas analyser.
13. The residual gas analyser according to clause 12, when dependent on clause 2, wherein the vacuum pump system comprises: a first vacuum pump configured to generate substantial vacuum conditions in the sample chamber; a second vacuum pump configured to generate substantial vacuum conditions in the ionisation chamber; and optionally, an interstage line between the first vacuum pump and the second vacuum pump.
14. The residual gas analyser according to clause 12 or 13, wherein the vacuum pump system is configured to generate a pressure in the sample chamber in the range 4 to 10 microbar.
15. The residual gas analyser according to any of clauses 12 to 14, wherein the vacuum pump system is configured to generate a pressures in the ionization chamber in the range 1 nanobar to 10 microbar.
16. The residual gas analyser according to any of clauses 12 to 15, wherein the ionization chamber comprises: a first pressure region that comprises the one or more ion sources; and a second pressure region that comprises the one or more detectors; wherein the second pressure region is at a lower pressure that the first pressure region.
17. The residual gas analyser according to clause 16, wherein the first pressure region of the ionization chamber is at the same pressure as the sample chamber.
18. The residual gas analyser according to clause 16 or 17, wherein the vacuum pump system is configured to generate a pressure in the second pressure region of the ionization chamber in the range 1 nanobar to 20 nanobar, and preferably less than 5 nanobar.
19. A vacuum tool comprising one or more residual gas analysers according to any preceding clause.
20. The vacuum tool according to clause 19, wherein the vacuum tool is an EUV vacuum tool or a source of an EUV vacuum tool.
21. The vacuum tool according to clause 19 or 20, wherein: the vacuum tool comprises one or more vacuum chambers; and each residual gas analyser is arranged to detect gas in a vacuum chamber.
22. The vacuum tool according to any of clauses 19 to 21, wherein the vacuum tool comprises a vacuum pump system arranged to generate a pressure in a vacuum chamber of the vacuum tool in the range 30 to 60 millibar.
23. A method of testing a residual gas analyser, the method comprising: using a gas generating filament to generate gas within the residual gas analyser; operating the residual gas analyser to detect the generated gas;

and determining the performance of the residual gas analyser in dependence on the detection of the gas.

24. The method according to clause 23, wherein the residual gas analyser is a residual gas analyser according to any of clauses 1 to 18.

25. A method of conditioning a residual gas analyser, the method comprising: radiating the inside of a sample chamber of the residual gas analyser by radiation generated by a gas generating filament in the sample chamber; and de-gassing the sample chamber.

26. The method according to clause 25, wherein the residual gas analyser is a residual gas analyser according to any of clauses 1 to 18.

27. A method of calibrating a residual gas analyser, the method comprising: using a gas generating filament to generate gas within the residual gas analyser; operating the residual gas analyser to detect the generated gas; and calibrating the residual gas analyser in dependence on the detected gas.

28. The method according to clause 27, wherein the residual gas analyser is a residual gas analyser according to any of clauses 1 to 18.

Although specific reference may be made in this text to embodiments of the invention in the context of a lithographic apparatus, embodiments of the invention may be used in other apparatus. Embodiments of the invention may form part of a mask inspection apparatus, a metrology apparatus, or any apparatus that measures or processes an object such as a wafer (or other substrate) or mask (or other patterning device). These apparatus may be generally referred to as lithographic tools. Such a lithographic tool may use vacuum conditions or ambient (non-vacuum) conditions.

The term "EUV radiation" may be considered to encompass electromagnetic radiation having a wavelength within the range of 4-20 nm, for example within the range of 13-14 nm. EUV radiation may have a wavelength of less than 10 nm, for example within the range of 4-10 nm such as 6.7 nm or 6.8 nm.

Although specific reference may be made in this text to the use of lithographic apparatus in the manufacture of ICs, it should be understood that the lithographic apparatus described herein may have other applications. Possible other applications include the manufacture of integrated optical systems, guidance and detection patterns for magnetic domain memories, flat-panel displays, liquid-crystal displays (LCDs), thin film magnetic heads, etc.

While specific embodiments of the invention have been described above, it will be appreciated that the invention may be practiced otherwise than as described. The descriptions above are intended to be illustrative, not limiting. Thus it will be apparent to one skilled in the art that modifications may be made to the invention as described without departing from the scope of the claims set out below.

The invention claimed is:

1. A residual gas analyzer for detecting gas in a vacuum tool, the residual gas analyzer comprising:
   one or more ion sources configured to ionize a gas in the residual gas analyzer;
   one or more detectors configured to detect an ionized gas by the one or more ion sources;
   one or more gas generating filaments configured to generate gas within the residual gas analyzer;
   a sample chamber configured to receive a gas from the vacuum tool;
   an ionization chamber configured to receive ionized gas from the sample chamber;
   a first vacuum pump configured to generate substantial vacuum conditions in the sample chamber;
   a second vacuum pump configured to generate substantial vacuum conditions in the ionization chamber;
   a first pressure region that comprises the one or more ion sources; and
   a second pressure region that comprises the one or more detectors;
   wherein the second pressure region is at a lower pressure than the first pressure region.

2. The residual gas analyzer of claim 1, wherein:
   the sample chamber comprises the one or more gas generating filaments;
   the ionization chamber comprises the one or more ion sources and the one or more detectors; and
   each ion source is arranged to emit ions into the sample chamber.

3. The residual gas analyzer of claim 1, wherein each gas generating filament comprises one or more of Rhenium, Tungsten, or Iridium.

4. The residual gas analyzer of claim 1, wherein each gas generating filament is configured to be heatable; and
   each gas generating filament releases gas when it is heated.

5. The residual gas analyzer of claim 1, wherein each gas generating filament is configured to be heatable by an electric current.

6. The residual gas analyzer of claim 2, further comprising:
   a sample tube configured to provide a flow path of gas from the vacuum tool to the sample chamber; and
   a valve in the flow path configured to control the flow of gas through the sample tube.

7. The residual gas analyzer of claim 1, wherein at least one of the one or more detectors comprises a mass analysis instrument.

8. The residual gas analyzer of claim 1, wherein at least one of the one or more detectors comprises one or more of a quadruple mass filter, a Faraday cup, and a secondary electron multiplier detector.

9. The residual gas analyzer of claim 1, wherein at least one of the one or more ion sources comprises at least two ion generating filaments.

10. The residual gas analyzer of claim 1, further comprising:
    an inter-stage line between the first vacuum pump and the second vacuum pump.

11. The residual gas analyzer of claim 10, wherein the first vacuum pump is configured to generate a pressure in the sample chamber in the range 4 to 10 microbar.

12. The residual gas analyzer of claim 10, wherein the second vacuum pump is configured to generate a pressure in the ionization chamber in the range 1 nanobar to 10 microbar.

13. The residual gas analyzer of claim 1, wherein the first pressure region of the ionization chamber is at a same pressure as the sample chamber.

14. The residual gas analyzer of claim 13, wherein a vacuum pump system is configured to generate a pressure in the second pressure region of the ionization chamber in the range 1 nanobar to 20 nanobar, and preferably less than 5 nanobar.

15. A method of testing the residual gas analyzer of claim 1, the method comprising:
    using the one or more gas generating filaments to generate gas within the residual gas analyzer;

operating the residual gas analyzer to detect the generated gas; and determining the performance of the residual gas analyzer in dependence on the detection of the gas.

16. A method of conditioning the residual gas analyzer of claim 1, the method comprising:

generating radiation using the gas generating filaments in the sample chamber to radiate an inside of the sample chamber of the residual gas analyzer; and de-gassing the sample chamber.

17. A method of calibrating the residual gas analyzer of claim 1, the method comprising:

using the one or more gas generating filaments to generate gas within the residual gas analyzer;

operating the residual gas analyzer to detect the generated gas; and calibrating the residual gas analyzer in dependence on the detected gas.

* * * * *

UNITED STATES PATENT AND TRADEMARK OFFICE
CERTIFICATE OF CORRECTION

PATENT NO. : 12,326,428 B2
APPLICATION NO. : 18/032438
DATED : June 10, 2025
INVENTOR(S) : Jilisen et al.

Page 1 of 1

It is certified that error appears in the above-identified patent and that said Letters Patent is hereby corrected as shown below:

In the Claims

In Column 17, Claim 16, Line 7, delete "the" and insert -- the one or more --, therefor.

Signed and Sealed this
Fifteenth Day of July, 2025

Coke Morgan Stewart
*Acting Director of the United States Patent and Trademark Office*